United States Patent [19]

Moberg

[11] Patent Number: 4,686,990
[45] Date of Patent: Aug. 18, 1987

[54] BATTERY TEST CIRCUIT FOR A HEART PACEMAKER

[75] Inventor: Lennart Moberg, Spanga, Sweden

[73] Assignee: Siemens Aktiengesellschaft, Berlin and Munich, Fed. Rep. of Germany

[21] Appl. No.: 908,213

[22] Filed: Sep. 17, 1986

[30] Foreign Application Priority Data

Oct. 2, 1985 [DE] Fed. Rep. of Germany ....... 3535181

[51] Int. Cl.⁴ .......................... A61N 1/02; A61N 1/36
[52] U.S. Cl. ...................... 128/419 PT; 128/419 PS; 128/419 PG; 128/697
[58] Field of Search .................. 128/419 PT, 419 PS, 128/419 PG, 697

[56] References Cited

U.S. PATENT DOCUMENTS

| 3,599,627 | 8/1971 | Millen . |
| 3,618,615 | 11/1971 | Greatbatch . |
| 3,841,336 | 10/1974 | Daynard ........................ 128/419 PT |
| 4,102,346 | 7/1978 | Fulker ........................... 128/419 PT |
| 4,231,027 | 10/1980 | Mann et al. . |
| 4,276,883 | 7/1981 | McDonald et al. ........... 128/419 PT |
| 4,445,512 | 5/1984 | Krupka et al. ............... 128/419 PT |
| 4,527,567 | 7/1985 | Fischler et al. .............. 128/419 PG |
| 4,556,061 | 12/1985 | Barreras et al. .............. 128/419 PT |

OTHER PUBLICATIONS

Siemens brochure for Multi-Programmable Pulse Generator Models 668 and 678.

Primary Examiner—William E. Kamm
Assistant Examiner—Timothy Keegan
Attorney, Agent, or Firm—Hill, Van Santen, Steadman & Simpson

[57] ABSTRACT

A battery test circuit for a heart pacemaker generates a signal which corresponds to the charge status of the pacemaker battery which is displayable in a manner which does not interfere with the normal pacing frequency of the pacemaker. A marking pulse is generated by the circuit at a chronological position between successive stimulation pulses which is dependent upon the charge status of the battery at the time the marking pulse is generated.

4 Claims, 7 Drawing Figures

BATTERY TEST CIRCUIT FOR A HEART PACEMAKER

RELATED APPLICATION

This application is related to another application of Lennart Moberg entitled "Battery Test Circuit For A Heart Pacemaker" filed simultaneously herewith and identified with U.S. Ser. No. 908,212.

BACKGROUND OF THE INVENTION

The present invention relates to heart pacemakers, and in particular to a circuit for monitoring and displaying the charge status of the pacemaker battery.

It is known in pacemaker technology to display the charge status of the battery of the pacemaker at the time of testing by emitting a plurality of test pulses having a frequency dependent upon the charge status. The frequency of the test pulses can be identified by ECG technology. Generation of such test pulses, however, requires that the therapeutically set stimulation frequency must be altered during the test mode.

It is an object of the present invention to provide a heart pacemaker with a battery status test circuit which generates a simple analog display of the charge status of the battery without altering the frequency of the stimulation pulses which are normally supplied by the pacemaker.

The above object is achieved in accordance with the principles of the present invention in a battery status test circuit which includes means for generating an electrical signal which corresponds to the charge status of the battery, the signal in turn driving a pulse generator which generates at least one display pulse at the output of the pacemaker. The circuitry also includes means for chronologically positioning the display or marking pulse relative to the stimulation pulses, depending upon the charge status of the battery at the time of testing. The charge status of the battery can thereby be read from the ECG signals without disturbing normal stimulation of the heart. Display of the charge status can be undertaken in two ways. In a first embodiment, the marking pulse is emitted in each interval between two successive stimulation pulses, as long as the pacemaker is activated for reading out the charge status of the battery, i.e., is in a test mode. The position of the marking pulse relative to the preceding or following stimulation pulse indicates the charge status. In another embodiment, a marking pulse with a position dependent upon the charge status of the battery is emitted in every $n^{th}$ interval, where n is a whole number and the position of the marking pulse in the interval determines the decimal point following this whole number. A high display precision is thereby achieved.

DESCRIPTION OF THE PREFERRED EMBODIMENTS

Figure 1:
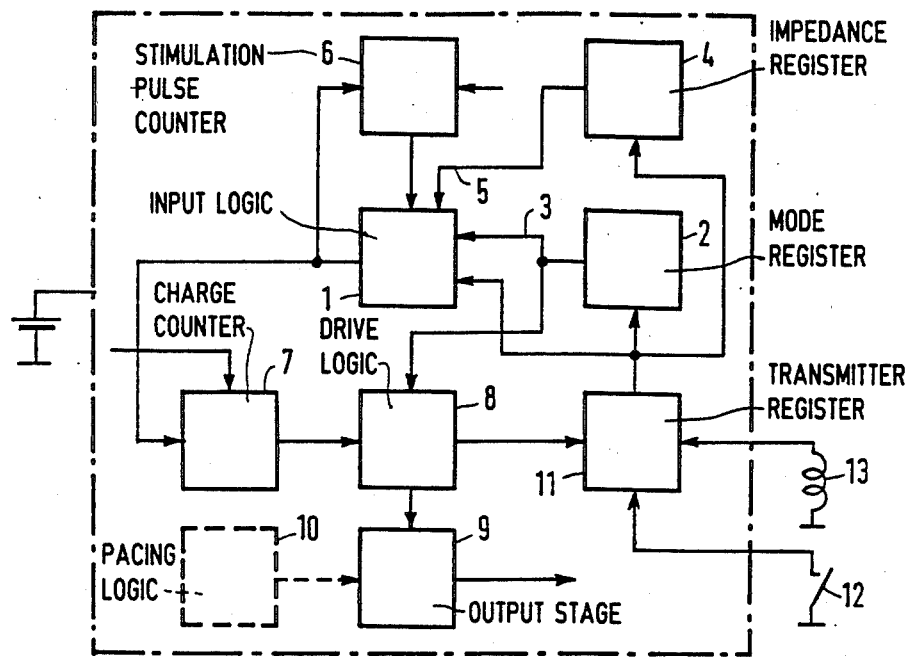
FIG. 1 is a schematic block diagram of a battery status test circuit for a heart pacemaker constructed in accordance with the principles of the present invention.

The basic components of one embodiment of a battery charge status test circuit constructed in accordance with the principles of the present invention are shown in FIG. 1. A signal corresponding to the set therapeutic values of the heart pacemaker is supplied to input logic 1 at an input 3 from a mode register 2. An impedance register 4 supplies a signal to the input logic 1 corresponding to the electrode impedance at another input 5. The number of stimulation pulses generated since a last battery status test are counted in a stimulation pulse counter 6. A charge counter 7 stores an electrical signal corresponding to the charge status of the battery, this electrical signal driving an output stage 9 via drive logic 8. The output stage 9 is connected to the pacing logic 10. The circuit is driven by a transmitter/receiver 11. The transmitter/receiver 11 can be actuated by a magnetically actuatable contact 12, or can be actuated wirelessly by a coil 13. Signals are supplied to the contact 12 or the coil 13 by an external transmitter/receiver.

When the circuit of FIG. 1 is activated (i.e., placed in the test mode) by the transmitter/receiver 11, the therapeutic values of the heart pacemaker, such as pulse amplitude, pulse duration and stimulation frequency, are supplied to the input logic 1. Using these signals, the electrode impedance signal, and information regarding basic patient consumption, the input logic 1 calculates the charge which has been consumed which may be expressed, for example, in basic units 5μAh. The stimulationpulses which have been incremented since the last test, and which the stimulation pulse counter 6 supplies to the input logic 1, are also taken into consideration for this calculation. The consumed charge is summed in the charge counter 7. The content of the charge counter 7, therefore, is a measure of the charge consumed. This signal is mixed into the output signal of the heart pacemaker via the drive logic 8 and the output stage 9, as described in greater detail below.

Figure 2:
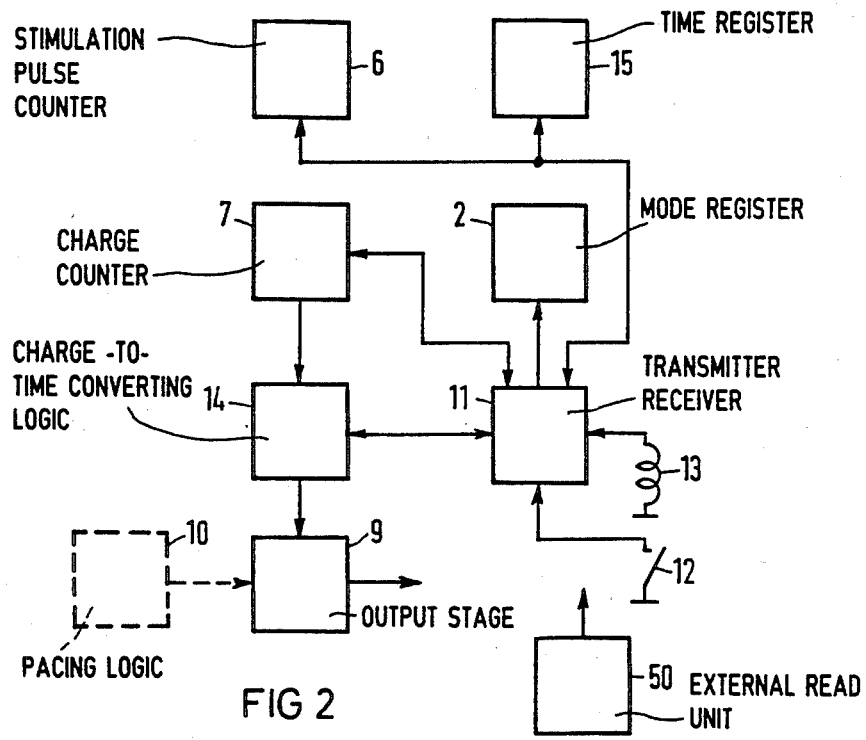
FIG. 2 is a further embodiment of the battery test status circuit constructed in accordance with the principles of the present invention.

In the embodiment of FIG. 2, components identical to those described above are provided with the same reference symbol. In addition to the components of FIG. 1, the embodiment of FIG. 2 includes a time register 15, charge-to-time converting logic 14, and the mode register 2, the stimulation pulse counter 6, and the charge counter 7 are interconnected differently from the embodiment in FIG. 1. In the embodiment of FIG. 2, during a test mode, an external read unit 50 first reads the time register 15. The time register 15 then supplies an electrical signal corresponding to the time of the measurement at a predetermined period of, for example, 2 hours. This means that the time register 15 generates a new signal every 2 hours.

With the knowledge of the time of the measurement, the external read unit 50 can identify the fundamental battery consumption. After making this calculation, the external unit 50 reads the current value of the stimulation pulse counter 6, which constitutes the number of stimulation pulses since the last battery test. If the stimulation pulse counter 6 has a current value of zero, it is known that the charge counter 7 is charged only with the fundamental consumption.

If the stimulation pulse counter 6 has a current value differing from zero, the external unit 50 executes the following steps. First, registers for the pulse amplitude, pulse duration and stimulation frequency (not shown) are read. The external unit 50 then calculates the electrode impedance. With these values, the external unit 50 can calculate the charge consumption of each stimulation pulse by a table. This consumption is multiplied by the number of stimulation pulses in the current reading of the stimulation pulse counter 6, and is added to the fundamental consumption. Subsequently, the charge counter 7 is charged with this value and the stimulation pulse counter 6 is reset to zero.

Each time the pacemaker is re-programmed in a manner which influences the consumption, a battery test is undertaken.

For forming an electrical signal corresponding to the remaining battery capacity, the charge-to-time coverting logic 14 converts the value of the charge counter 7 into a signal corresponding to the remaining battery life. This time can be read via the transmitter/receiver 11, however, it is also possible to mix the signal with the normal pacemaker output signal in the output stage 9 as described below.

Figure 3:
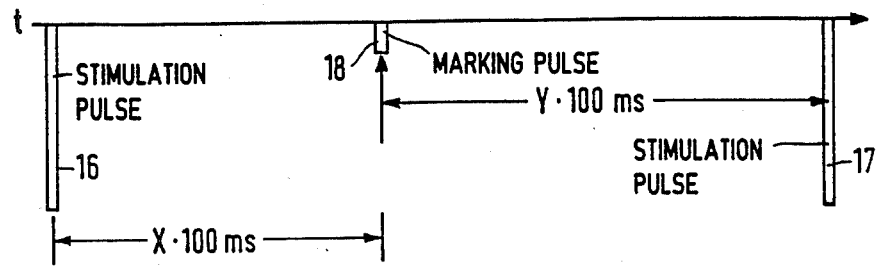
FIG. 3 is one type of output display indicating battery charge status in accordance with the principles of the present invention.

One manner of displaying the battery status signal is shown in FIG. 3. In this embodiment, two successive stimulation pulses 16 and 17 of the pacemaker are shown, with a marking pulse 18 mixed therewith. The marking pulse 18 is generated by the output stage 9. The chronological spacing of the marking pulse 18 from the stimulation pulse 16 depends upon the residual capacity of the battery still remaining and, as shown in FIG. 3, amounts to x times 100 ms or y times 100 ms. Either one of the values x or y corresponds to the remaining battery capacity in years. The marking pulse 18 is mixed with the stimulation pulse signal only in the test mode. During this time, the pacemaker operates with a fixed frequency.

Figure 4:
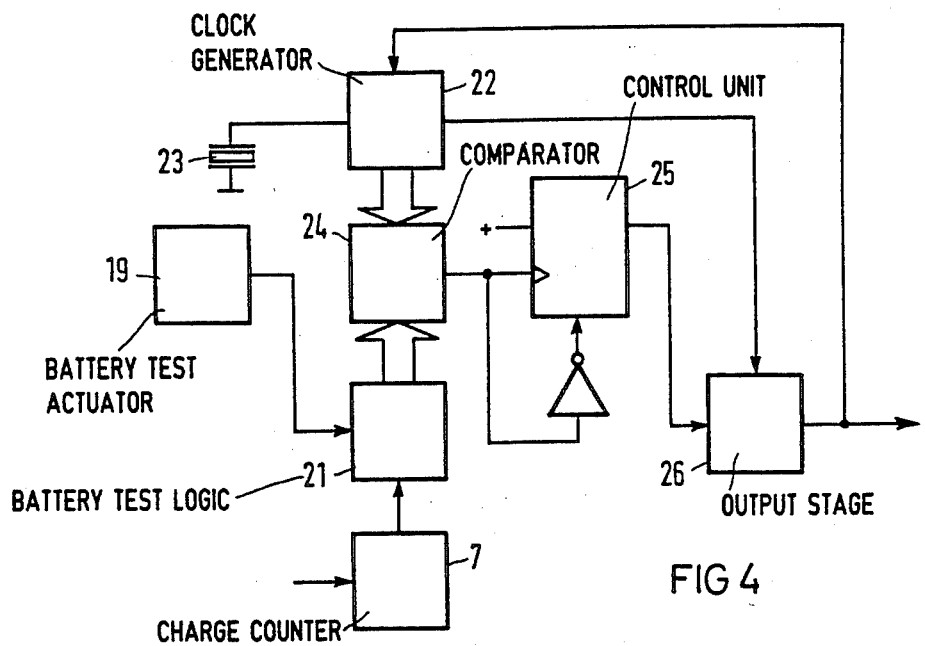
FIG. 4 is a schematic block diagram of a circuit for generating the output sequence shown in FIG. 3.

Circuitry for generating the sequence shown in FIG. 3 is schematically represented in FIG. 4. This circuitry includes a battery test actuator 19 which drives battery test logic 21. The battery test logic 21 is supplied with the contents of the charge counter 7. The value from the charge counter 7 is converted in the battery test logic 21 into a time value, which corresponds to the remaining battery capacity in years (x or y). The value x or y is converted to a distance for the marking pulse 18 from the stimulation pulse 16 or the stimulation pulse 17, which amounts to x or y times 100 ms. The value in the battery test logic 21 is compared in a comparator 24 with a time base which is supplied by a clock generator 22 connected to an oscillator 23. The result of the comparison determines the correct position of the marking pulse 18 with respect to the stimulation pulse 16 or 17, and the marking pulse is mixed with the output pulses of the pacemaker via a control stage 25 and an output stage 26.

Figure 5:
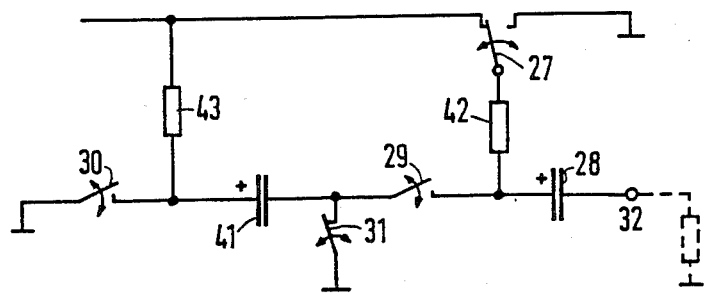
FIG. 5 is a circuit diagram for the output stage of the circuit shown in FIG. 4.

The output stage 26 schematically shown in FIG. 4 is shown in detail in FIG. 5. During normal operation, a switch 27 assumes the position shown in FIG. 5. During the charging phase of an output capacitor 28, the switches 29 and 30 are opened and the switch 31 is closed. For generating an output pulse, the switches 29 and 30 are closed and the switch 31, which was previously closed, is opened. As a result, a stimulation pulse is generated at the output 32.

As stated above, the pacemaker operates with a fixed frequency during the test mode. When the value in the battery test logic 21 is equal to the value of the time base generated by the clock generator 22, the switch 27 is briefly switched, for example for a duration of 1 ms. The components of the circuit of FIG. 5 are dimensioned such that the amplitude of the marking pulse generated is not sufficient to stimulate the heart.

Figure 6:
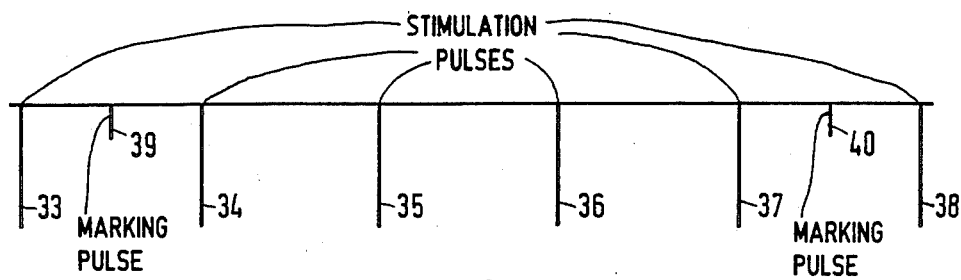
FIG. 6 is another type of pulse sequence for indicating the charge status of the battery generated in accordance with the principles of the present invention.

Another type of display mode which can be obtained in accordance with the principles of the present invention is shown in FIG. 6. In this embodiment, stimulation pulses 33 through 38 are supplied by the pacemaker during the test mode at a fixed frequency. Marking pulses, such as pulses 39 and 40, are generated at locations which are x times 100 ms after the respective preceding stimulation pulses 33 and 37, or y times 100 ms before the respective following stimulation pulses 34 and 38. The marking pulse 40 appears in the $n^{th}$ interval after the preceding marking pulse 33. In the example shown in FIG. 6, $n=7$ and $x=y=4$, indicating the remaining capacity of the battery is greater than 7.4 years.

Figure 7:
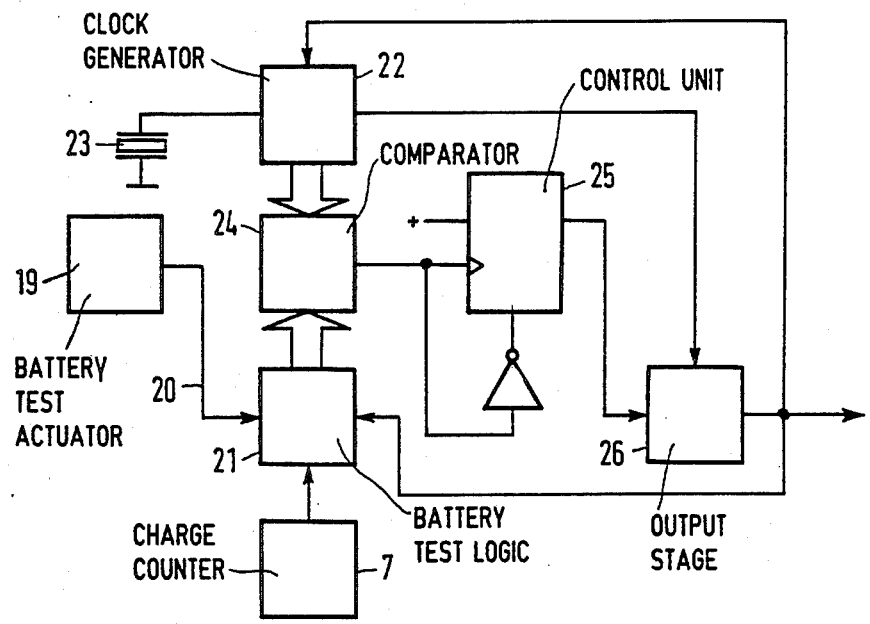
FIG. 7 is a schematic block diagram of a battery charge status test circuit constructed in accordance with the principles of the present invention for generating an output sequence a shown in FIG. 6.

The marking pulses 39 and 40 are generated by the circuit of FIG. 7, wherein components identical to the circuit of FIG. 4 are given the same reference symbols.

During a battery test, the value stored in the charge counter 7 is divided into a plurality of intervals which must be traversed before the marking pulse 40 is generated. When the correct interval arrives, the marking pulse 39 is first generated in the correct position in the interval. An output stage is already described in FIG. 5 is employed for this purpose. In this output stage, the switch 27 is always in the position indicated in the drawing when no battery test is being undertaken. During the charging phase of the output capacitor 28, switches 29 and 30 are opened and the switch 31 is closed. Capacitors 28 and 41 are charged by resistors 42 and 43.

A marking pulse is generated by closing the switches 29 and 30 and opening the switch 31. The output amplitude of the marking pulse is again selected such that stimulation of the heart does not occur, and the heart pacemaker frequency is fixed during the test mode. The value in the battery test logic 21 is compared to the time base. When the values are identical, i.e., when the correct time interval appears and the correct number of stimulation pulses have occurred since the marking pulse 39, the marking pulse 40 is generated by the switch 27. This marking pulse also does not stimulate the heart.

Although modifications and changes may be suggested by those skilled in the art it is the intention of the inventor to embody within the patent warranted hereon all changes and modifications as reasonably and properly come within the scope of his contribution to the art.

I claim as my invention:

1. A battery test circuit for a heart pacemaker which generates a plurality of successive stimulation pulses comprising:
   means for generating an electrical signal corresponding to the charge status of the battery;
   means for generating at least one marking pulse; and
   means for mixing said marking pulse with said stimulation pulses with the marking pulse disposed at a chronological position with respect to at least one of said stimulation pulses which corresponds to said charge status.

2. A battery test circuit as claimed in claim 1, wherein said means for mixing mixes said marking pulse with said stimulation pulses with said marking pulse disposed at a selected distance between two successive stimulation pulses, said selected distance corresponding to said charge status.

3. A battery test circuit as claimed in claim 1, wherein said means for generating at least one marking pulse generates said marking pulse after each $n^{th}$ stimulation pulse, wherein n is a whole number, and wherein said means for mixing mixes said marking pulse with said stimulation pulses with said marking pulse disposed at a chronological position with respect to said $n^{th}$ stimulation pulse corresponding to a remaining fraction of said charge status, such that n plus said remaining fraction is equal to the remaining battery capacity.

4. A battery test circuit as claimed in claim 3, wherein n is measured in years.

* * * * *